United States Patent [19]

Uhing et al.

[11] 4,100,230

[45] Jul. 11, 1978

[54] PROCESS FOR PREPARING MONO- AND DISUBSTITUTED MERCAPTO-PHOSPHOROTHIONO-CHLORIDATES

[75] Inventors: Eugene H. Uhing, Pleasantville, N.Y.; Arthur D. F. Toy, Stamford, Conn.

[73] Assignee: Stauffer Chemical Company, Westport, Conn.

[21] Appl. No.: 711,769

[22] Filed: Aug. 4, 1976

[51] Int. Cl.² .................................................. C07F 9/20
[52] U.S. Cl. ........................................ 260/972; 260/960
[58] Field of Search ................. 260/972, 960, 974, 981

[56] References Cited

U.S. PATENT DOCUMENTS

| | | | |
|---|---|---|---|
| 2,407,279 | 9/1946 | Hull et al. | 260/980 |
| 2,506,310 | 5/1950 | Mikeska | 260/980 |
| 2,622,095 | 12/1952 | Brannock | 260/981 |

FOREIGN PATENT DOCUMENTS 184,846  10/1966  U.S.S.R. ........................... 260/960

*Primary Examiner*—Anton H. Sutto
*Attorney, Agent, or Firm*—Ellen P. Trevors

[57] ABSTRACT

Mono- and disubstituted mercaptophosphorothionochloridates are prepared by reacting a disubstituted sulfide having the formula $$R_2S$$

wherein each R is an independently selected alkyl, cycloalkyl or benzyl, with phosphorus pentasulfide and thiophosphorus trichloride at a temperature from about 150° to about 300° C. A molar ratio of $R_2S$ to $P_4S_{10}$ to $P(S)Cl_3$ of 6:1:8 is preferred where the monosubstituted compound is desired, while a ratio of 6:1:2 is preferred where the disubstituted compound is desired. The compounds are useful as intermediates for compounds which exhibit biocidal properties, particularly insecticides and herbicides.

14 Claims, No Drawings

PROCESS FOR PREPARING MONO- AND DISUBSTITUTED MERCAPTO-PHOSPHOROTHIONOCHLORIDATES

BACKGROUND OF THE INVENTION

This invention relates to a process for preparing various mono- and disubstituted mercaptophosphorothionochloridates.

The substituted mercaptophosphorothionochloridates are known compounds having utility as intermediates for the preparation of agricultural chemicals, such as insecticides and herbicides.

Various processes for preparing certain substituted mercaptophosphorothionochloridates have been described in the prior art. The following reaction schemes are typical of these processes:

$$P(S)Cl_3 + RSH \rightarrow RSP(S)Cl_2 + HCl \qquad (1)$$

$$RSPCl_2 + S \rightarrow RSP(S)Cl_2 \qquad (2)$$

These prior art processes are described in detail in *Methoden Der Organischen Chemie*, Band XII/1, Teil I pages 682–683 and 739–740 (1963) published by Georg Thieme Verlag, Stuttgart, Germany. While providing the desired compounds, these prior art processes have been found to be undesirable in that yields are often low and substantial amounts of undesirable by-products are formed.

U.S. Pat. No. 3,879,500 issued Apr. 22, 1975 to Eugene H. Uhing and Arthur D. F. Toy describes a process for preparing these compounds employing an appropriate chloride as a reactant, while U.S. Pat. No. 2,836,534 issued May 27, 1958 to Gail H. Birum teaches the preparation of some of the monosubstituted compounds from sulfenyl chloride and a phosphorus sulfide.

SUMMARY OF THE INVENTION

Now it has been found in accordance with this invention that various mono- and disubstituted mercaptophosphorothionochloridates can be readily provided by reacting an appropriate disubstituted sulfide with phosphorus pentasulfide ($P_4S_{10}$) and thiophosphorus trichloride ($PSCl_3$). More particularly, the compounds prepared accordingly to the process of this invention have the following general formula:

$$(RS)_xP(S)Cl_{(3-x)} \qquad (I)$$

wherein each R is an independently selected alkyl, cycloalkyl or benzyl and $x$ is 1 or 2. The alkyl groups contain from 1 to 12 carbon atoms, and the term "alkyl" in the claims and specifications herein includes both n-alkyl and secondary alkyl groups. Exemplary alkyl groups are methyl, ethyl, i-propyl, i-butyl, n-butyl and dodecyl. The cycloalkyl groups have from 3 to 7 ring carbon atoms and include cyclopropyl, cyclohexyl, cycloheptyl, etc.

The reactions to provide the desired compounds proceed according to the following equations, where equation (3) provides the monosubstituted compounds and equation (4) provides the disubstituted compounds.

$$6 R_2S + P_4S_{10} + 8 P(S)Cl_3 \rightarrow 12 RSP(S)Cl_2 \qquad (3)\text{-}(II)$$

$$6 R_2S + P_4S_{10} + 2 P(S)Cl_3 \rightarrow 6 (RS)_2P(S)Cl \qquad (4)\text{-}(II)$$

Although stoichiometric amounts of reactants are generally employed, excesses of one or more reactants can be employed if desired. In reaction (3), it is generally preferred to use a stoichiometric excess of $P(S)Cl_3$ to minimize formation of the corresponding disubstituted compound.

It should be noted that where mixed sulfides, that is sulfides having the formula $R_2S$ where the R groups are different, are employed, mixtures of products are obtained. Thus, the product of the reaction illustrated in equation (3) can comprise two different compounds having the formula II, differing in the R groups resulting from the two different R groups in the sulfide. Similarly, the product of the reaction of equation (4) can comprise two different compounds III, and can also comprise a mixed disubstituted compound having the formula III and containing two different R groups.

Exemplary sulfides suitable for use in the process of this invention include: $(CH_3)_2S$; $(C_4H_9)_2S$; $(C_{12}H_{25})_2S$; $(C_3H_7)_2S$; $(C_7H_{15})_2S$; $(C_6H_5CH_2)_2S$; $(CH_3)(C_{12}H_{25})S$; $(CH_3)(C_7H_{15})S$; and $(C_4H_9)(C_6H_5CH_2)S$.

The process of this invention is carried out at elevated temperatures, generally between about 150° and 300° C; and preferably between about 180° and 250° C. The selected temperature will depend upon the particular sulfide used as a reactant and upon the time the reaction will be run. Generally, higher reaction temperatures require a shorter reaction time and conversely, lower reaction temperatures require a longer reaction time. The time of reaction and the appropriate temperature can be readily determined by one skilled in the art. However, typical reaction times vary from about 1 to about 24 hours and preferably from about 2 to about 12 hours.

The reaction can be run at atmospheric pressures with some reactants, and at superatmospheric pressures when so desired. However, it is the feature of the process of this invention that autogenous pressure be employed. Thus, pressure vessels such as metal bombs, autoclaves, and the like can be used. The process can be carried out in a continuous or batch-type operation.

The reactions are preferably carried out in a single step. However, if desired multi-step processes can be employed under the same reaction conditions described above. For example, the reaction according to equation (4) can be carried out stepwise by first reacting the $R_2S$ with $P_4S_{10}$ to form $(RS)_3PS$ as described in our copending application, U.S. Ser. No. 650,488, filed Jan. 19, 1976. This reaction is illustrated by equation (5).

$$6 R_2S + P_4S_{10} \rightarrow 4 (RS)_3PS \qquad (5)$$

The $(RS)_3PS$ thus obtained is then reacted with $PSCl_3$ according to the following equations wherein the disubstituted compound is prepared in equation (6) and the monosubstituted in equation (7).

$$4(RS)_3PS + 2PSCl_3 \rightarrow 6 (RS)_2P(S)Cl \qquad (6)$$

$$4(RS)_3PS + 8PSCl_3 \rightarrow 12 RSP(S)Cl_2 \qquad (7)$$

It is also within the scope of this invention to form the $PSCl_3$ reactant in situ by employing phosphorus trichloride and sulfur as reactants in any of the aforementioned reactions where $PSCl_3$ appears although this embodiment is not preferred.

The compounds prepared according to the process of this invention are obtained in good yields and are readily recovered by such conventional techniques as distillation, extraction, etc. Furthermore, it is a feature of this invention that the stoichiometry can be selected to provide either the monosubstituted or the disubstituted compounds, thereby enhancing the yield of desired product.

While any compounds having the formula I can be prepared according to this invention, it has been found that the process is particularly attractive for preparing compounds I where R is lower alkyl, that is alkyl having 1 to 4 carbon atoms, and $x$ is 2. Where the disubstituted compounds are prepared, it is most preferable to provide the aforementioned compounds where the R groups are the same.

The following examples will serve to illustrate the practice of this invention. When mole % by nmr spectroscopy is reported, it is based on uncorrected area %.

EXAMPLE 1

Preparation of $(CH_3S)_2P(S)Cl$

In a 300 ml. 316 stainless steel autoclave were placed 62.0 grams (1.00 mole) of $(CH_3)_2S$, 74.0 grams (0.166 mole) of $P_4S_{10}$ and 56.0 grams (0.333 mole) of $PSCl_3$. The autoclave was heated at 200° C for 8 hours. After cooling, a pour out yield of 179.5 grams of crude liquid reaction mixture was obtained. Analysis by $^{31}$P-nmr spectroscopy indicated that the following components were present in the reaction mixture:

$(CH_3S)_2P(S)Cl$ — 63 mole %
$CH_3SP(S)Cl_2$ — 15 mole %
$(CH_3S)_3PS$ — 22 mole %

The crude product was distilled to provide 95 grams of $(CH_3S)_2P(S)Cl$ boiling at 70°–80° C, 0.03mm Hg.

EXAMPLE 2

Example 1 was repeated with the exception that the reaction was carried out at 220° C. Analysis by $^{31}$P-nmr spectroscopy indicated that the reaction mixture contained 49 mole % $(CH_3S)_2P(S)Cl$, 13 mole % $CH_3SP(S)Cl_2$, and 26 mole % $(CH_3S)_3PS$.

EXAMPLE 3

Repeating Example 1 but carrying out the reaction at 250° C resulted in a reaction mixture containing 7 mole % $(CH_3S)_2PSCl$, 19 mole % $CH_3SP(S)Cl_2$ and 6 mole % $(CH_3S)_3PS$ as analyzed by $^{31}$P-nmr spectroscopy. While some product was obtained, it was concluded that the reaction temperature was too high for this particular reaction, resulting in product decomposition.

EXAMPLE 4

Preparation of $C_2H_5SP(S)Cl_2$

In a 300 ml. stainless steel autoclave were placed 45 grams (0.5 mole) of $(C_2H_5)_2S$, 37 grams (0.0833 mole) of $P_4S_{10}$ and 187 grams (1.1 moles) of $PSCl_3$. The autoclave was heated at 200° C for 8 hours. After cooling, the reaction mixture was poured out and distilled to provide 145 grams of liquid having a boiling range of 55°–120° C at 0.05 mmHg. Redistillation (45°–50° C at 0.01 mmHg) provided 100 grams of pure product; $n_D{}^{25}$ = 1.5890. Analysis of the pure product by $^{31}$P-nmr showed a shift from $H_3PO_4$ at $-69.6$ ppm, confirming that $C^2H_5SP(S)Cl_2$ has been obtained.

EXAMPLE 5

Preparation of n-$C_4H_9SP(S)Cl_2$

Example 4 was repeated with the exception that 73 grams (0.5 mole) of $(n-C_4H_9)_2S$ was employed as a reactant instead of the $(C_2H_5)_2S$. Redistillation provided a 66 mole % yield of n-$C_4H_9SP(S)Cl_2$ ($n_D{}^{25}$ = 1.5655; b.p. 60° C at 0.05 mmHg) according to $^{31}$P-nmr spectroscopy.

EXAMPLE 6

Preparation of $(C_2H_5S)_2P(S)Cl$

Following the procedure of the preceding Examples, 90 grams (1.0 mole) of $(C_2H_5)_2S$; 74 grams (0.166 mole) $P_4S_{10}$ and 62 grams (0.36 mole) $PSCl_3$ were reacted at 190° C for 10 hours. Analysis of the crude reaction product by $^{31}$P-nmr spectroscopy indicated that the following components were present:

$(C_2H_5S)_2P(S)Cl$ — 73.9 mole %
$C_2H_5SP(S)Cl_2$ — 15.7 mole %
$(C_2H_5S)_3PS$ — 10.4 mole %

The crude reaction product was distilled twice to provide a 47% by weight yield of $(C_2H_5S)_2P(S)Cl$, $n_D{}^{25}$ = 1.6052, which assayed at 93 mole % by $^{31}$P-nmr analysis.

EXAMPLE 7

Preparation of n-$C_8H_{17}SP(S)Cl_2$

Following the procedure of the preceding Examples, 64.5 grams (0.25 mole) of $(n-C_8H_{17})_2S$, 18.5 grams (0.0416 mole) of $P_4S_{10}$ and 90 grams (0.53 mole) of $PSCl_3$ were reacted at 190° C for 10 hours. The crude reaction mixture was distilled twice to provide 68 grams (49% yield) of n-$C_8H_{17}SP(S)Cl_2$ having the following properties:

b.p. at 0.01 mm = 110° C
$^{31}$P-nmr = $-69.0$ ppm
$n_D{}^{25}$ = 1.5308

EXAMPLE 8

Preparation of $C_6H_5CH_2SP(S)Cl_2$

Following the procedure and employing the reaction temperature and reactants of Example 7 with the exception that 53.5 grams (0.25 mole) of $(C_6H_5CH_2)_2S$ were employed as a reactant instead of $(n-C_8H_{17})_2S$, 68 grams (53% yield) of $C_6H_5CH_2SP(S)Cl_2$ was obtained. The product had the following properties:

b.p. at 0.01 mm = 105° C
$^{31}$P-nmr = $-76.6$ ppm
H-nmr confirmed the presence of the benzyl group
$n_D{}^{25}$ = 1.6382

EXAMPLE 9

Preparation of n-$C_3H_7SP(S)Cl_2$

The amount of 59 grams (0.5 mole) of $(n-C_3H_7)_2S$, 37 grams (0.0833 mole) $P_4S_{10}$ and 186 grams (1.1 moles) $PSCl_3$ were reacted at 190° C for 9 hours in a 300 ml. autoclave. The resulting reaction mixture was distilled twice to provide a 65 mole % yield of n-$C_3H_7SP(S)Cl_2$, b.p. 35° C at 0.05 mm, $n_D{}^{25}$ = 1.5771. Confirmation of the structure of the product was obtained by nmr spectroscopy (H, C and P).

EXAMPLE 10

Preparation of i-C₃H₇SP(S)Cl₂

Example 9 was repeated but employing 59 grams of (i-C₃H₇)₂S as the sulfide reactant and carrying out the reaction at 155° C. A 47 mole % yield of i-C₃H₇SP(S)Cl₂, b.p. 35° C at 0.05 mm, $n_D^{25}=1.5711$, was obtained. The nmr spectra (H, C and P) confirmed the structure of the product.

When this experiment was repeated at 190° C, excessive amounts of HCl formed, indicating that lower reaction temperatures are preferable for this synthesis.

EXAMPLE 11

Preparation of (CH₃)₂CHCH₂SP(S)Cl₂

Following the procedure of the previous Examples, 24.9 grams (0.17 mole) of ((CH₃)₂CHCH₂)₂S was reacted with 12.5 grams (0.0283 mole)P₄S₁₀ and 62.6 grams (0.37 mole) PSCl₃. The reaction was carried out at 180° C for 9 hours. A 50 mole % yield of (CH₃)₂CHCH₂SP(S)Cl₂, bp 45° C at 0.05mm, $n_D^{25}=$ 1.5628, was obtained. The nmr spectra (H, C and P) confirmed the structure of the product.

COMPARATIVE EXAMPLE 1

Repetition of Example 11 but employing ((CH₃)₃C)₂S as the disulfide gave a complex mixture of products with only a trace amount of (CH₃)₃CSP(S)Cl₂.

COMPARATIVE EXAMPLE 2

Employing (C₆H₅)₂S as the sulfide reactant in Example 11 provided almost no distillable material.

EXAMPLE 12

C₂H₅SP(S)Cl₂ Recycle Process

In a 300 ml 316 ss autoclave having a 1000 psi gauge were placed 45 grams (0.5 mole) of (C₂H₅)₂S, 37 grams (0.0833 mole) of P₄S₁₀ and 187 grams (1.1 moles) of PSCl₃. The autoclave was heated to 200° C for 8 hours; the pressure gauge read 20 psi at 200° C. After cooling the autoclave was vented; the vent gas contained 0.11 moles HCl. A pour out yield of 256 grams of crude product was obtained. Distillation of the crude product at 12 mm provided 69 grams PSCl₃ boiling at 70° C and at 0.05 mm provided 116 grams of C₂H₅SP(S)Cl₂, $n_D^{25}=1.5907$. The distillation was stopped and the pot residue weight was 52 grams.

For the second cycle, the autoclave was charged with ½ the starting weights used in the first cycle plus the 52 gram pot residue and the 69 grams of PSCl₃ obtained from the first cycle. Using the same reaction conditions as for the first cycle, a pour out yield of 256 grams was obtained. Distillation provided 78 grams PSCl₃ and 93 grams of C₂H₅SP(S)Cl₂, leaving a 64 gram pot residue.

Then the 64 grams of pot residue was further treated in the autoclave with 159 grams of PSCl₃ at 200° C for 8 hours. Distillation of the reaction mixture provided 135 grams of PSCl₃ and 16 grams of C₂H₅SP(S)Cl₂. The total yield of C₂H₅SP(S)Cl₂ was 225 grams (77 mole % yield). The ³¹P-nmr spectra of the final pot residue revealed 12 different phosphorus components.

EXAMPLE 13

Preparation of (C₂H₅S)₂P(S)Cl

This example illustrates the two-step process of this invention.

In a 300 ml stainless steel autoclave were placed 27.0 grams (C₂H₅)₂S (0.3 mole) and 22.2 grams P₄S₁₀ (0.05 mole). The autoclave was heated at 240° C for 12 hours. After cooling, a pour out yield of 46 grams of curde product was obtained. Distillation provided 20 grams of product having a boiling range of 110°–175° C at 0.1 mm Hg; $n_D^{20}=1.6169$. The product was analyzed by ³¹P-nmr spectroscopy which showed chemical shifts from H₃PO₄ at −92.4 ppm and −91.9 ppm, indicating the presence of (C₂H₅S)₃P(S).

In a 150 ml. test tube were placed 2.69 grams (0.01 mole) of the (C₂H₅S)₃P(S) as prepared in the preceding paragraph and 3.38 grams (0.02 mole) of PSCl₃. The test tube was stopped loosely with a cork and placed in an oil bath heated to 130° C. The temperature of the bath was raised to 160° C over 45 minutes and the test tube was kept in the bath for an additional 15 minutes at the bath temperature of 160° C. Analysis of the resultant product by ³¹P-nmr showed a shift from H₃PO₄ at −69.5 ppm, confirming that about 5 mole % of (C₂H₅S)₂P(S)Cl had been obtained.

EXAMPLE 14

Preparation of C₂H₅SP(S)Cl₂

Following the procedure and employing the apparatus of Example 13, 5.38 grams (0.02 mole) of (C₂H₅S)₃PS were reacted with 1.69 grams (0.01 mole) PSCl₃. Analysis of the product by ³¹P-nmr spectroscopy showed a 15–20 mole % yield of C₂H₅SP(S)Cl₂ (shift at −93.0 ppm).

What is claimed is:

1. A process for preparing a compound having the formula:

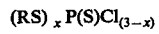

$$(RS)_x P(S)Cl_{(3-x)}$$

where each R is an independently selected alkyl, cycloalkyl or benzyl, and $x$ is 1 or 2, comprising; reacting a sulfide reactant having the formula R₂S wherein R is as defined above, with P₄S₁₀ and P(S)Cl₃ at a temperature of from about 150° C to about 300° C, and recovering the $(RS)_x P(S)Cl_{(3-x)}$.

2. The process of claim 1 wherein R is lower alkyl and $x$ is 1.

3. The process of claim 2 wherein said sulfide reactant is diethyl sulfide.

4. The process of claim 2 wherein said sulfide reactant is di-n-propyl sulfide.

5. The process of claim 2 wherein said sulfide reactant is di-i-propyl sulfide.

6. The process of claim 2 wherein said sulfide reactant is di-n-butyl sulfide.

7. The process of claim 2 wherein said sulfide reactant is di-i-butyl sulfide.

8. The process of claim 1 wherein R is benzyl and $x$ is 1.

9. The process of claim 1 wherein R is lower alkyl and $x$ is 2.

10. The process of claim 9 wherein sulfide reactant is dimethyl sulfide.

11. The process of claim 9 wherein said sulfide reactant is diethyl sulfide.

12. The process of claim 1 wherein a temperature of from about 180° to about 250° C is employed.

13. A process for preparing a compound having the formula:

$$(RS)_xP(S)Cl_{(3-x)}$$

where each R is an independently selected alkyl, cycloalkyl or benzyl, comprising; reacting a sulfide reactant having the formula $R_2S$ with $P_4S_{10}$ to provide $(RS)_3PS$, and then reacting said $(RS)_3PS$ with $PSCl_3$, said R groups being as described above and said reactions being carried out at a temperature of from about 150° to about 300° C, and recovering the $(RS)_xP(S)Cl_{(3-x)}$.

14. The process according to claim 1, wherein the byproducts obtained in the process are recycled and reacted with said $P_4S_{10}$ and $P(S)Cl_3$ to provide additional compound of the formula:

$$(RS)_xP(S)Cl_{(3-x)}$$

wherein R and $x$ are as described in claim 1.

* * * * *

UNITED STATES PATENT AND TRADEMARK OFFICE
CERTIFICATE OF CORRECTION

PATENT NO. : 4,100,230
DATED : July 11, 1978
INVENTOR(S) : Eugene H. Uhing and Arthur D. F. Toy It is certified that error appears in the above-identified patent and that said Letters Patent are hereby corrected as shown below:

Col. 1, line 27 - "Verlag" should be "Verlug".
Col. 1, line 66 - "(11)" should be "(III)".
Col. 6, line 10 - "curde" should be "crude".

Col. 6, line 20 - "stopped" should be "stoppered".

Col. 6, line 65 - "said" omitted from "wherein said sulfide reactant".

Signed and Sealed this

Sixth Day of February 1979

[SEAL]

Attest:

RUTH C. MASON
Attesting Officer

DONALD W. BANNER
Commissioner of Patents and Trademarks